United States Patent
Dafni et al.

(10) Patent No.: US 8,121,250 B2
(45) Date of Patent: Feb. 21, 2012

(54) METHOD FOR CALIBRATION OF A CT SCANNER

(75) Inventors: Ehud Dafni, Caesarea (IL); Olga Shapiro, Haifa (IL); David Ruimi, Ganot Hadar (IL)

(73) Assignee: Arineta Ltd., Caesarea (IL)

( * ) Notice: Subject to any disclaimer, the term of this patent is extended or adjusted under 35 U.S.C. 154(b) by 207 days.

(21) Appl. No.: 12/698,185

(22) Filed: Feb. 2, 2010

(65) Prior Publication Data

US 2010/0195804 A1  Aug. 5, 2010

Related U.S. Application Data

(60) Provisional application No. 61/206,425, filed on Feb. 2, 2009.

(51) Int. Cl.
*G01D 18/00* (2006.01)
*G01N 23/00* (2006.01)

(52) U.S. Cl. .................................. 378/18; 378/207
(58) Field of Classification Search .............. 378/4, 9, 378/18, 204, 205, 207
See application file for complete search history.

(56) References Cited

U.S. PATENT DOCUMENTS

| | | | |
|---|---|---|---|
| 4,352,020 A | 9/1982 | Horiba et al. | |
| 5,214,578 A | 5/1993 | Cornuejols et al. | |
| 5,481,587 A * | 1/1996 | Mazess | 378/207 |
| 5,774,519 A | 6/1998 | Lindstrom et al. | |
| 6,148,057 A | 11/2000 | Urchuk et al. | |
| 6,364,529 B1 * | 4/2002 | Dawson | 378/207 |
| 6,848,827 B2 | 2/2005 | Wu et al. | |
| 6,944,258 B2 | 9/2005 | Nukui et al. | |
| 7,149,277 B2 | 12/2006 | Tanigawa et al. | |
| 7,738,624 B2 * | 6/2010 | Herold et al. | 378/18 |

* cited by examiner

*Primary Examiner* — Irakli Kiknadze

(57) ABSTRACT

A method for calibration of a CT comprises sequentially positioning a phantom having a non-circular cross section and a length commensurate with the extent of a detector at a plurality of positions between an X ray source and the detector array or sequentially positioning a plurality of generally similar phantoms or sequentially positioning a same phantom at a plurality of positions between the X ray source and detector array of the CT scanner; acquiring calibration attenuation data for X rays that have been attenuated by traversing the phantom positioned at each of the plurality of positions; and calculating calibration corrections for CT scanner scan data from the calibration attenuation data.

33 Claims, 8 Drawing Sheets

METHOD FOR CALIBRATION OF A CT SCANNER

RELATED APPLICATIONS

This application claims the benefit of priority of U.S. Provisional Patent Application No. 61/206,425, filed on Feb. 2, 2009, the contents of which are incorporated herein by reference.

FIELD OF THE INVENTION

The invention is in the field of imaging by X-Ray Computerized Tomography (CT). More specifically, the invention provides a method for calibration of CT scanners and correction of data acquired by CT scanners.

BACKGROUND OF THE INVENTION

Computerized Tomography (CT) scanners produce images of a subject by reconstruction of X ray attenuation data acquired over multiple view angles. Various corrections are applied to the measured raw data in order to obtain artifact free images which are true representation of the scanned subject. Some of these corrections are based on calibration processes, in which calibration measurements performed on the scanner are used to generate calibration tables and corresponding corrections.

One example of such calibration is known in the art as "air calibration". Typically, air calibration involves performing a scan using a CT scanner, without there being a subject or phantom in the imaging space between the X ray source and the detector, so the detector array is irradiated by un-attenuated X ray beam. The acquired date, sometimes termed "air calibration data" is indicative of the relative efficiency and gain of the detector array elements and the variation in X ray beam intensity across the irradiation field. The air calibration data is used to normalize the attenuation data acquired during a subject scan.

Other effects that require calibration and correction are related to X ray beam hardening. Typical X ray sources used in CT scanners emit X radiation having a wide spectrum of energies. Since low energy X-ray photons are attenuated by matter more strongly than high energy photons, the spectrum of the radiation is changes as the radiation traverse the subject. The average X-ray energy of the transmitted beam increases for larger penetration lengths of the beam in the subject. Thus, the attenuation coefficient is relatively higher for thin than for thick paths. Since the thickness of the patient is different for different portions of a patient beam hardening gives rise to a phenomenon known as "cupping", whereby an image of a cross section in a homogenous cylinder does not look like a flat disk but rather exhibits apparently lower attenuation values in the center.

Another phenomenon related to the beam hardening is a resulted imbalance between the output signals of different detector elements. The detector elements are normalized using air calibration data which are measured at one beam spectrum. However, the detection efficiency depends on the X-ray energy and this dependence is somewhat different from element to element. Therefore, different detector elements may response somewhat differently to X radiation of different spectra. Therefore, air calibration does not accurately normalize the attenuation data measured for a thick subject. In a third generation (rotate-rotate) CT scanner, imbalance between the output signals of neighboring detector elements results in artifacts known in the art as "rings", "bands" and "bulls-eye".

These phenomena and other non-linear effects are corrected in CT scanners by using calibration data derived from measurements on phantoms. Phantoms are objects of known composition and shape. One approach to the calibration known in the art and described e.g. in U.S. Pat. No. 4,352,020 to Horiba et al, is to scan a set of cylindrical phantoms of different diameters centered about the rotation center of the scanner and generate calibration tables based on the difference between the measured data and the data expected under ideal conditions. In subsequent subject scans, calibration tables are used to calculate correction factors depending on the attenuation level for each detector element. In order for the calibration process to be effective, the range of attenuations observed by each detector element in phantoms scans should generally correspond to the range of attenuation that would be observed by that detector element in a subject scan. For example, in a medical CT, detector elements in the center of the detector array typically observe higher attenuation than side detector elements. Calibration measurements on a set of cylinders made of organic polymer such as polypropylene, covering a range of diameters corresponding to small, medium and large human bodies would provide a satisfactory set of calibration tables.

U.S. Pat. No. 5,214,578 to Cornuejos et al. describes a method for calibration of a CT scanner using a cylindrical phantom placed off the isocenter (rotation axis) of the scanner. The advantages of phantom positioned off center are twofold: there is no need for tedious accurate positioning of the phantom at the center and the range of attenuation levels measured by each detector element during a rotational scan is increased, so measurements on a single phantom may potentially be sufficient. Yet, there are practical limitations in actual cases. Considering for example a scanner with a bore inner diameter of 600 mm, a cylindrical phantom of 400 mm diameter can be shifted at most by 100 mm from the bore center and the center detector elements are shaded by phantom thickness of 346-400 mm during a scanner rotation, not covering the lower attenuation levels expected to occur in clinical scans. Therefore, in certain cases the use of multiple phantoms may still be used. However, there is no teaching of how such phantoms are used.

U.S. Pat. No. 5,774,519 to Lindstrom et al, describes a system in which multiple phantoms are used. It appears that these phantoms are centered at the same position.

U.S. Pat. No. 6,848,827 to Xiaoye et al describes a system in which multiple cylindrical phantoms of different diameters are used. These phantoms are placed off the center of rotation by an amount that depends on the diameter of the phantom.

U.S. Pat. No. 6,944,258 to Nukui et al., all describe different methods for calculation and application of image corrections based on calibration measurements based on one or multiple phantoms positioned at a same position off the isocenter.

U.S. Pat. No. 7,149,277 to Tanigawa et al discloses a method for calculating correction coefficients using measurements on phantom having an oblong cross section or a cross section of an annular sector, from multiple directions. Also in this case the calibration may involve measurement of several phantoms of different sizes and shapes. Phantoms of oblong cross section have the advantage of presenting different penetration length from different view angles and thus increasing the range of attenuation levels observed during a rotational scan.

U.S. Pat. No. 6,148,057 to Urchuk et al. proposes a different approach, wherein the calibration of differences between detector elements are determined by measurements on slab absorbers of several thicknesses. The slab thickness may vary by stacking layers or by incrementing forward a step like phantom. These measurements do not involve rotation of the CT gantry but rather acquisition from a direction substantially normal to the slabs. Variations of this method include using an absorber of variable thickness respective the azimuthal direction of the scanner fan beam rather than a flat slab.

In any of the calibration methods it is desired to calibrate the scanner at the same X-ray attenuation range that is generally observed subject scans. For human body imaging, the center of the detector should be calibrated at the attenuation range approximately equivalent to absorption of 150 mm to 400 mm of water. Further, it is desired to use calibration phantoms with a chemical composition similar to that of a human body so that beam hardening effects in the phantom will simulate the beam hardening effects in a patient properly.

In modern CT scanners the number of detector rows in the axial direction is generally larger than in the past. Commercially available CT scanners with pixilated two dimensional detector arrays currently have up to 320 rows of detectors, covering an axial length of 160 mm at the isocenter of the scanner and over 200 mm at the periphery of the field of view. Other CT scanners known as "cone beam scanners" use a flat panel detector as the detector array and the axial coverage may be even higher. Therefore a calibration process based on a set of cylindrical or slab phantoms would require the use of cylinders, oblong objects or slabs, each over 200 mm thick in the axial direction. As a result, calibration phantoms according to any of the methods known in the art applied to wide beam CT scanners are heavy, difficult to handle and expensive.

SUMMARY OF THE INVENTION

The present invention is concerned with methods of calibrating CT scanners and phantoms for use in these methods.

In an aspect of some embodiments of the invention phantoms are placed at multiple positions between the x-ray source and the detector array and attenuation data is acquired. This data is used to generate correction values for scan data as a function of the measured attenuation.

There is thus provided, in accordance with a preferred embodiment of the invention, method for calibration of a CT scanner having an x-ray source and a detector having an axial extent in the scanner, the source being rotatable about an epicenter between the source and detector, the method comprising:

sequentially positioning a phantom having a non-circular cross section and a length commensurate with the extent of the detector at a plurality of positions between the X ray source and detector array of said CT scanner or sequentially positioning a plurality of phantoms each having a non-circular cross section and a length commensurate with the extent of the detector at a plurality of positions between the X ray source and detector array of said CT scanner;

acquiring calibration attenuation data for X rays that have been attenuated by traversing the phantom positioned at each of said plurality of positions; and calculating calibration corrections for CT scanner scan data from said calibration attenuation data.

Optionally, the plurality of phantom positions comprises more than two positions.

Optionally, the calibration attenuation data are acquired at multiple rotation angles of the source for at least one of said multiple phantom positions.

Optionally, the calibration data are acquired while the X ray source of said CT scanner is static during acquisition of said calibration attenuation data.

Optionally, the calibration data are acquired while the X ray source of said CT scanner is rotating about the scanner rotation axis during acquisition of said calibration attenuation data.

Optionally, calibration data for different parts of the detector array are calculated from calibration attenuation data acquired at different phantom positions.

Optionally, a same phantom or different ones of a plurality of phantoms having essentially a same cross-section are placed at said plurality of positions used to obtain calibration tables for said CT scanner.

Optionally, a plurality of phantoms of different cross-section are used to obtain calibration tables for said CT scanner.

Optionally, a phantom has an elliptical, triangular or asymmetric cross section.

Optionally, the phantom is positioned to within better than 1 mm or 2 mm relative to the rotation axis of said CT scanner.

Optionally, the phantom position is determined from the attenuation data.

Optionally, the calibration corrections correct scan data for differences in the response of detector elements to X-rays.

Optionally, the calibration corrections correct scan data for X-rays beam hardening effects and/or for dependence of the response of said scanner detection system to the attenuation level of said X radiation.

Optionally, at least a plurality of said positions are offset from said epicenter of the CT scanner.

There is further provided, in accordance with a further preferred embodiment of the invention, a method for calibration of a CT scanner having an x-ray source and a detector array, the source being rotatable about an epicenter between the source and the detector, the method comprising:

sequentially positioning a same phantom or a plurality of essentially similar such phantoms at a plurality of positions between the X ray source and detector array of said CT scanner;

sequentially positioning a same phantom having a length commensurate with the extent of the detector at a plurality of positions between the X ray source and detector array of said CT scanner or sequentially positioning a plurality of essentially similar phantoms and a length commensurate with the extent of the detector at a plurality of positions between the X ray source and detector array of said CT scanner;

acquiring calibration attenuation data for X rays that have been attenuated by traversing the phantom positioned at each of said plurality of positions; and calculating calibration corrections for CT scanner scan data from said calibration attenuation data.

Optionally, the plurality of phantom positions comprises more than two positions.

Optionally, the calibration attenuation data are acquired at multiple rotation angles of the source for at least one of said multiple phantom positions.

Optionally, the calibration data are acquired while the X ray source of said CT scanner is static during acquisition of said calibration attenuation data.

Optionally, the calibration data are acquired while the X ray source of said CT scanner is rotating about the scanner rotation axis during acquisition of said calibration attenuation data.

Optionally, calibration data for different parts of the detector array are calculated from calibration attenuation data acquired at different phantom positions.

Optionally, a same phantom or different ones of a plurality of phantoms having essentially a same cross-section are placed at said plurality of positions used to obtain calibration tables for said CT scanner.

Optionally, a plurality of phantoms of different cross-section are used to obtain calibration tables for said CT scanner.

Optionally, a phantom has an elliptical, triangular, circular or asymmetric cross section.

Optionally, the phantom is positioned to within better than 1 mm or 2 mm relative to the rotation axis of said CT scanner.

Optionally, the phantom position is determined from the attenuation data.

Optionally, the calibration corrections correct scan data for differences in the response of detector elements to X-rays.

Optionally, the calibration corrections correct scan data for X-rays beam hardening effects and/or for dependence of the response of said scanner detection system to the attenuation level of said X radiation.

Optionally, at least a plurality of said positions are offset from said epicenter of the CT scanner.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

As used herein the term essentially similar means that two objects are substantially the same for the purposes of the calibration procedure.

DETAILED DESCRIPTION OF SOME EMBODIMENTS

Figure 1:
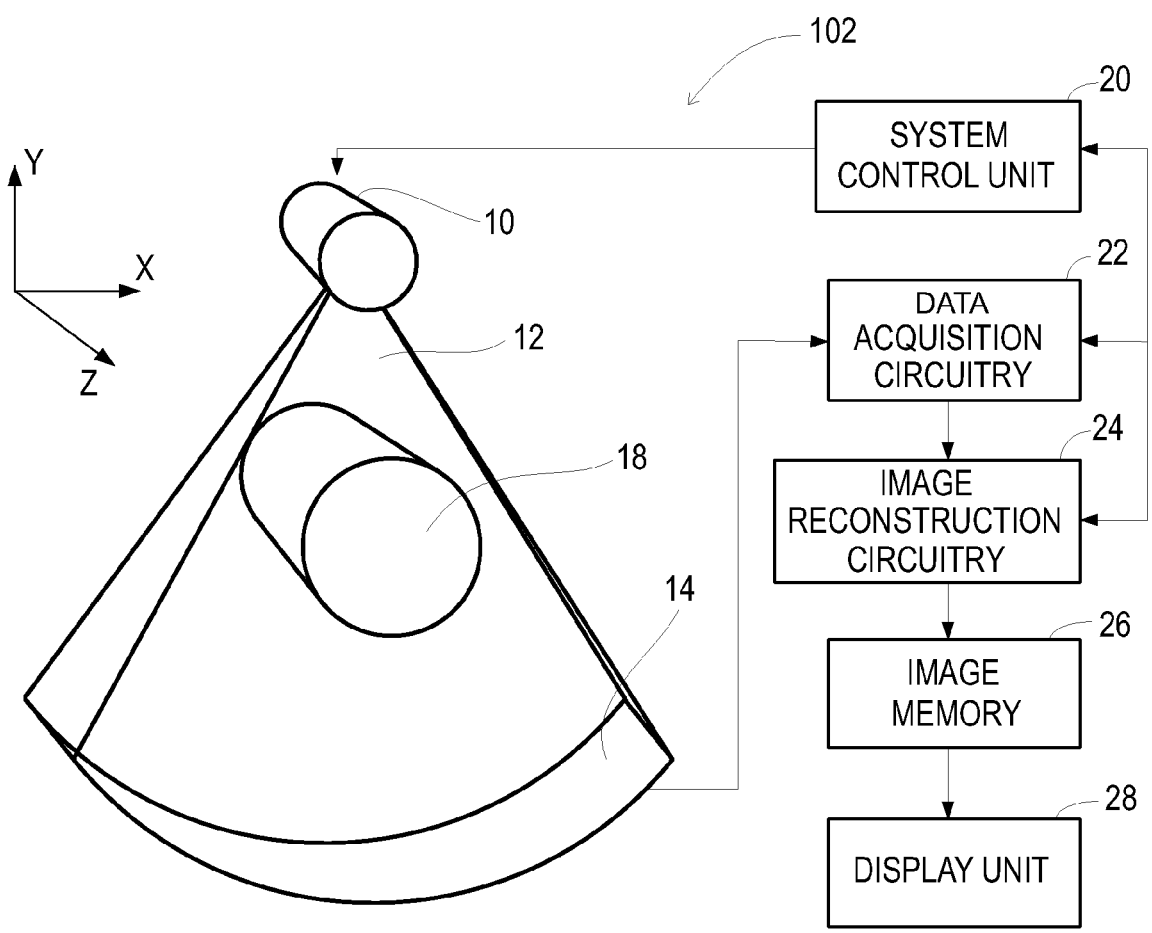
FIG. 1 is a schematic representation of a CT scanner with a cylindrical phantom of circular cross-section placed at the iso-center of rotation, as in the prior art.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

An aspect of some embodiments of the invention deals with methods of correcting for beam hardening and/or other attenuation related non-linearity effects on x-rays detection. An aspect of some embodiments of the invention deals with methods of correcting differences in the response of detector elements in a detector array to X rays of different energies.

In some embodiments the corrections are applied to CT scanners.

In some embodiments a single phantom or a plurality of individual or compound phantoms are sequentially placed in different positions within the region between the x-ray source and a detector array in a CT scanner. Attenuation data is acquired and compared to expected results to determine a correction factor for various attenuation levels. By using a plurality of positions of the phantom or phantoms and/or source angles a range of attenuation values that is greater than that in the prior art can be acquired, giving a more accurate correction.

The applicants have found that using a phantom with an elliptical or flattened circular cross-section (herein referred to collectively as elliptical) a wide range of attenuation values can be acquired when the phantom is imaged in multiple positions.

Other possible phantom combinations include circular phantoms that are identical or near identical placed in different positions in the field of detection of the detectors. Both asymmetric and symmetric phantoms can be used as well as phantoms of similar shape and different size, especially phantoms with a non-circular cross-section or circular phantoms placed at a plurality of positions off the central axis of the x-ray beam.

Before discussing the various embodiments of the present invention, it is helpful to review various methodologies of calibration of CT scanners as found in the prior art.

FIG. 1 is a schematic representation of a CT scanner 102 with a cylindrical phantom of circular cross-section placed at the iso-center of rotation, as in the prior art. An X ray source 10 emits a beam of X radiation 12 in the direction of a detector array 14. Typically the source-detector pair is mounted on a rotating gantry and a subject to be examined is positioned between the source and the detector. A cylindrical phantom of circular cross-section 18 is shown placed at the iso-center of rotation of the source and detector array. Detector array 14 may be composed of array of discrete elements arranged in rows and columns, a flat panel detector or other suitable detector as known in the art. It may have a spherical or arc shape centered about the focal spot (as shown), be planar or have other surface curvature. Herein below we refer to "rows" of the detector as the X direction of the detector perpendicular to the rotation axis (Z direction), i.e., the circumferential direction.

The coordinate system shown in FIG. 1 refer to the rotating gantry so the Z axis is parallel to the rotation axis and the Y axis points from the detector array to the X ray source at any rotation angle Various parts of CT scanner 102, including the gantry and patient support are not shown in FIG. 1 for simplification. In addition to the source, detector array, gantry and patient support, the system includes a system control unit 20 that controls movement of the patient table and rotation of the gantry as well as activation of the x-ray source. System control unit 20 also controls data acquisition circuitry 22 such that data is acquired in conjunction with x-ray irradiation and image reconstruction circuitry 24 which receives the data and information on the rotation angle of the x-ray source and detector array about the iso-center and reconstructs images therefrom. Image memory 26 and display unit 28 are provided for storage and display of images. Control unit 20 (or image reconstruction circuitry 24 or another memory in the system) contains various information on corrections to be made to the data to correct, inter alia, for variations between the detector elements and for beam hardening. This correction information may be generated on a theoretical basis or from calibration data as described below with respect to the prior art and various embodiments of the invention.

Further, a single source CT scanner 102 of rotate-rotate geometry (third generation), in which the source and detectors rotate together around the patient, is shown but the invention is applicable to other source and scanner geometries as well, for example dual source scanners, electron beam scanners, fourth generation scanners and other designs. While the CT scanner is described in conjunction with a particular prior art correction methodology, it should be understood that both the prior art methods of calibration and the methods of the present invention are applicable to each of these types of scanners.

In the following explanations of the prior art methods and those according to various embodiments of the present invention, the Figures do not show the detector array. Only the x-ray source, phantoms and ray traces of x-rays emitted by the source are shown, since these are sufficient to understand the invention.

Figure 2:
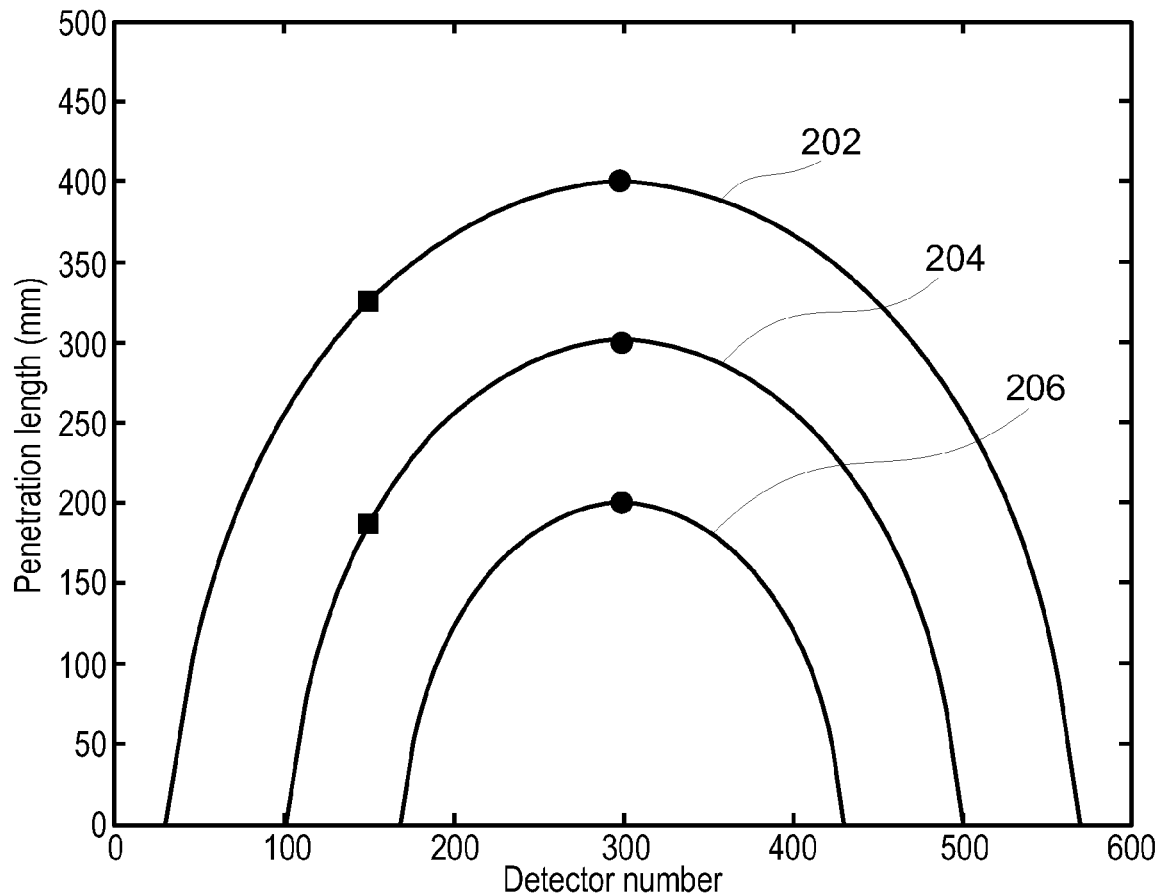
FIG. 2 shows expected penetration length as a function of detector number for centered cylindrical phantoms of circular cross-section for various diameters, as in one embodiment of the prior art.

A prior art method for calibration of CT scanners is based on measuring attenuation data on a set of cylindrical phantoms positioned sequentially at the center of the scan field of view. FIG. 2 shows expected radiation penetration length in the phantom as a function of detector number. Hereinbelow such graphs are referred to as "length profiles". In this example the distance of the X-ray focal spot to isocenter is 450 mm and there are 600 detector elements in each row of the detector array, covering angular span of 60°. The penetration length is measured in mm. Length profiles are shown for three calibration measurements: curves 202, 204 and 206 corresponding to measurements on phantoms of 400 mm, 300 mm and 200 mm diameter respectively, respectively. In this case of round, centered, phantoms, the calibration data may be acquired during gantry rotation or at a static gantry position, which would yield substantially the same results.

It should be understood that in the absence of non linear effects such as beam hardening, for a phantom made of homogenous material the log attenuation of the beam is proportional to the penetration length. Thus, if the log of actual measurements of attenuation with a phantom are compared to the length profile, a correction for the attenuation data can be derived. Further, differences in the spectral response between neighboring detection channels can be measured and corrected as well. Some types of artifacts are especially sensitive to differences in calibration between nearby detector elements.

In the calibration data of FIG. 2 detector elements at the center of the array receive three calibration data points at penetration length of 200 mm, 300 mm, and 400 mm. The calibration data points for detector element number 300 are marked in FIG. 2 by circles for identification. However, detector elements near the sides of the array receive only two or one (or near the edge, no) calibration points at lower penetration lengths. For example, detector element number 150 has only two calibration data points identified in FIG. 2 by square markings.

The calibration process by this method may be optimized for particular clinical applications by different choice of phantom diameters. Also the chemical composition, density and phantom internal structure may be optimized. Yet, the method provides only a limited range of penetration lengths, depending on detector position in the array, and requires handling of a set of phantoms. Some CT scanners with a single or limited number of detector rows use a single cylindrical phantom including steps with different radii. However, for a wide beam scanner each step has to be wide and a cylindrical step phantom solution is not practical for weight and cost reasons.

Figure 3A:
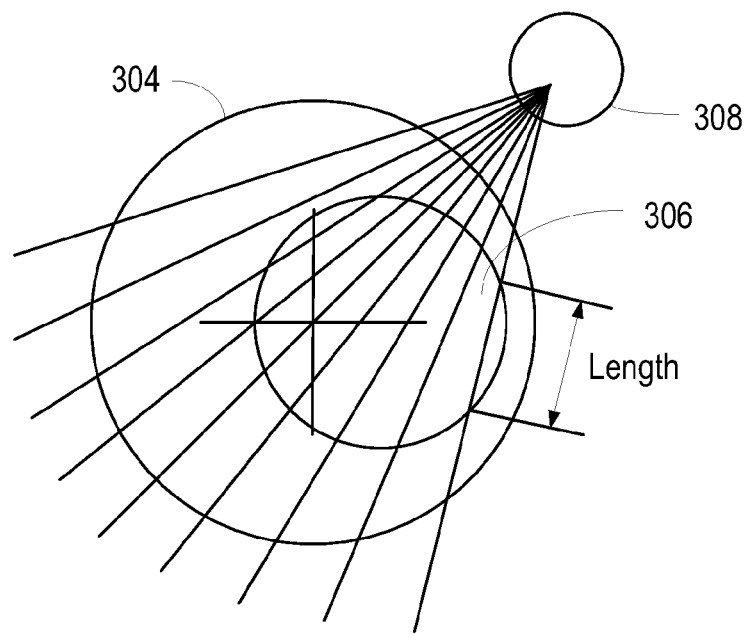
FIG. 3A schematically shows beam paths for an off-center cylindrical phantom with a circular cross-section for a second embodiment according to the prior art.
Figure 3B:
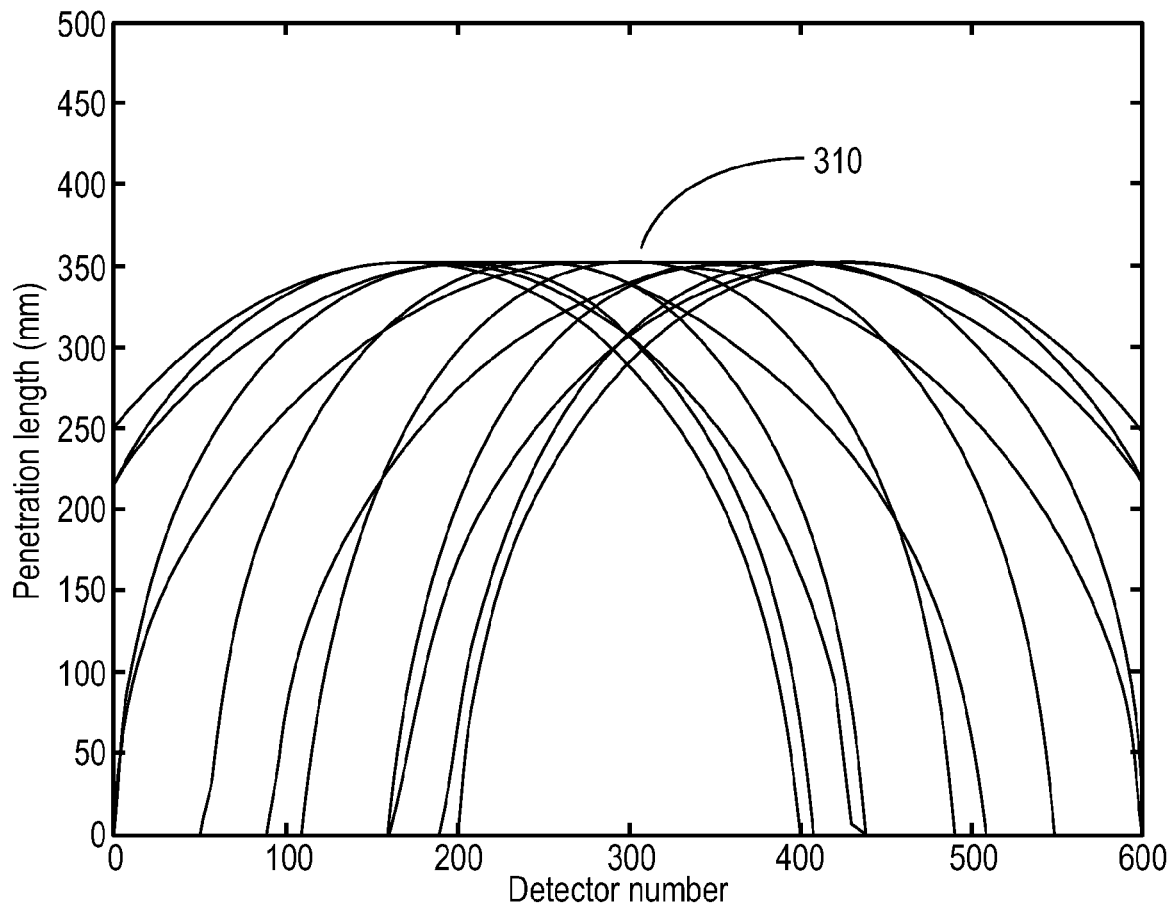
FIG. 3B shows expected penetration length as a function detector number for various angles of rotation of the source and detectors for the phantom configuration of FIG. 3A.

FIG. 3A provides the calibration measurement geometry for another prior art method wherein a cylindrical phantom 306 is shifted off center within the scanner bore 304. FIG. 3B provides the corresponding length profiles 310 measured at 12 gantry angles at angular increments of 30°. In this example phantom 306 has a diameter of 350 mm and is shifted 100 mm off center. The calibration measurement can be performed with a rotating radiation source 308, which provides a length profile for each view, or at a set of fixed angular positions respective the phantom 306. FIG. 3B shows length profiles for a limited number of views.

The calibration measurements described above with respect to FIG. 3A and FIG. 3B provide multiple calibration points at penetration length varying from zero to at or near the phantom diameter for side detectors, provided data is taken at sufficient number of source angular positions. However, for detector elements at the center of the array, calibration data is available only for penetration length in the range of about 280 mm to 350 mm, in this particular example. Lower penetration length measurements can be achieved for center detectors by using a smaller diameter phantom and larger shift off center but that would reduce the maximum length observed across the array.

Figure 4A:
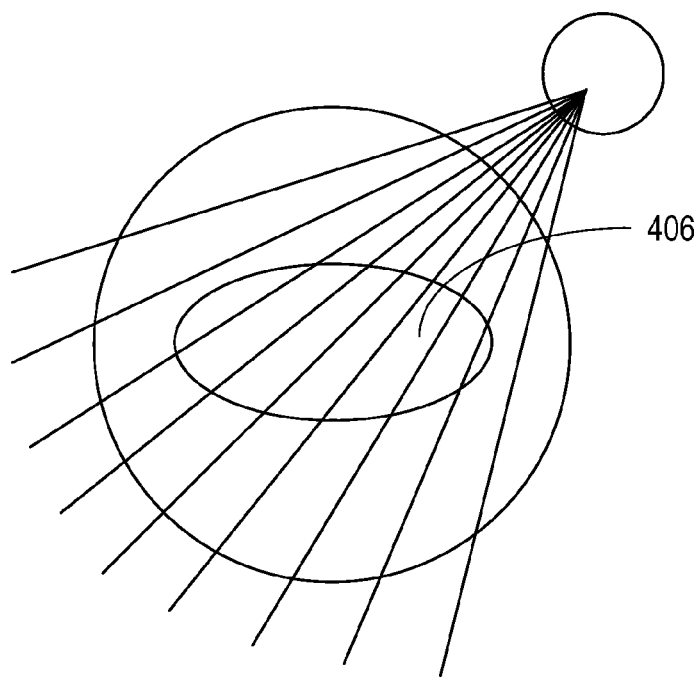
FIG. 4A schematically shows beam paths for a cylindrical phantom with an elliptical cross-section in a third embodiment according to the prior art.
Figure 4B:
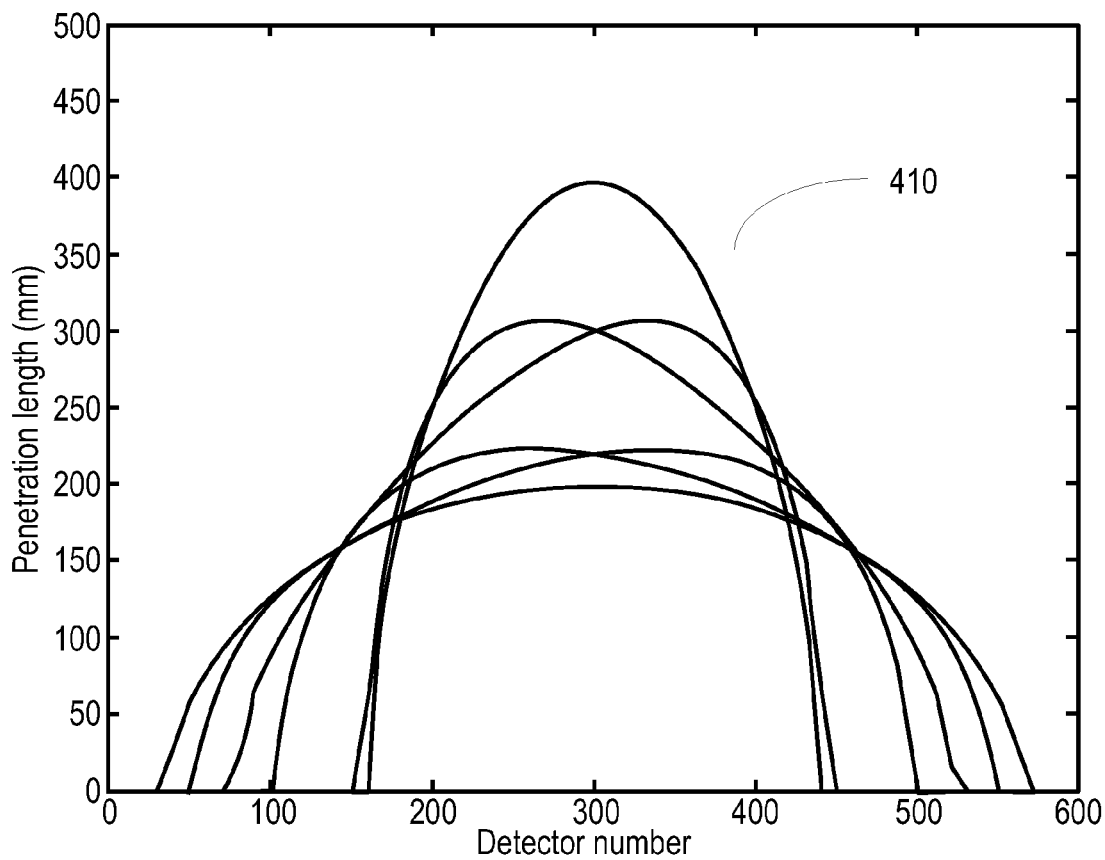
FIG. 4B shows expected penetration length as a function detector number for various angles of rotation of the source and detectors for the phantom configuration of FIG. 4A.

FIG. 4A and FIG. 4B illustrate a yet another prior art method. Calibration data corresponding to length profiles 410 are obtained using a phantom 406 of elliptical cross-section. In the example of FIG. 4A and FIG. 4B, phantom 406 is centered and has a minor axis of 200 mm and major axis of 400 mm. Length profiles 402 are shown for measurements at gantry angular rotation increments of 30°. The calibration method illustrated in FIG. 4a and FIG. 4b provides an adequate set of calibration points for the center detectors using a single phantom, but only a limited set of calibration points for side detector. This situation may be improved to a certain degree by positioning phantom 406 off center.

Figure 5:
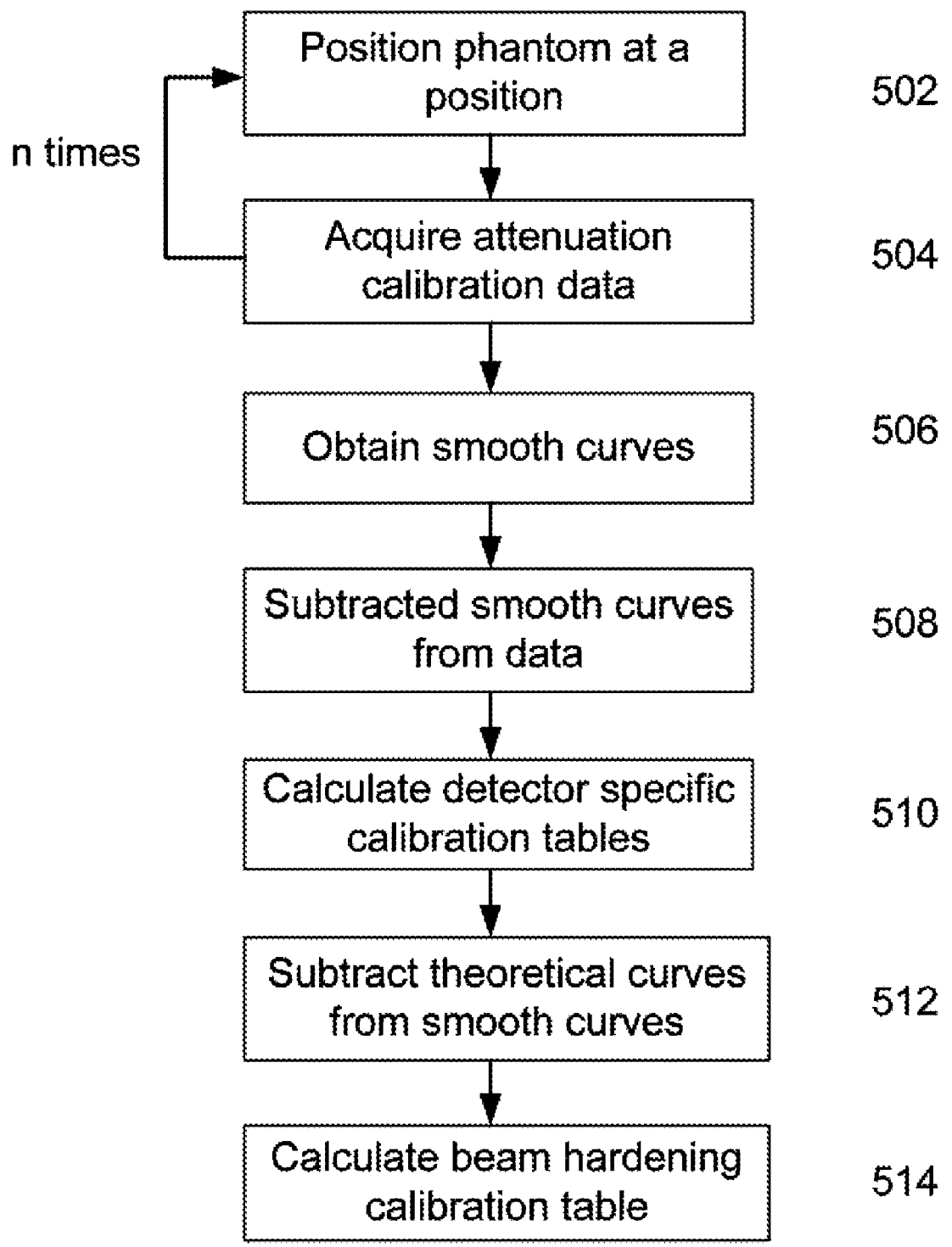
FIG. 5 is a flow diagram for a method of calibration, in accordance with some embodiments of the present invention.
Figure 6A:
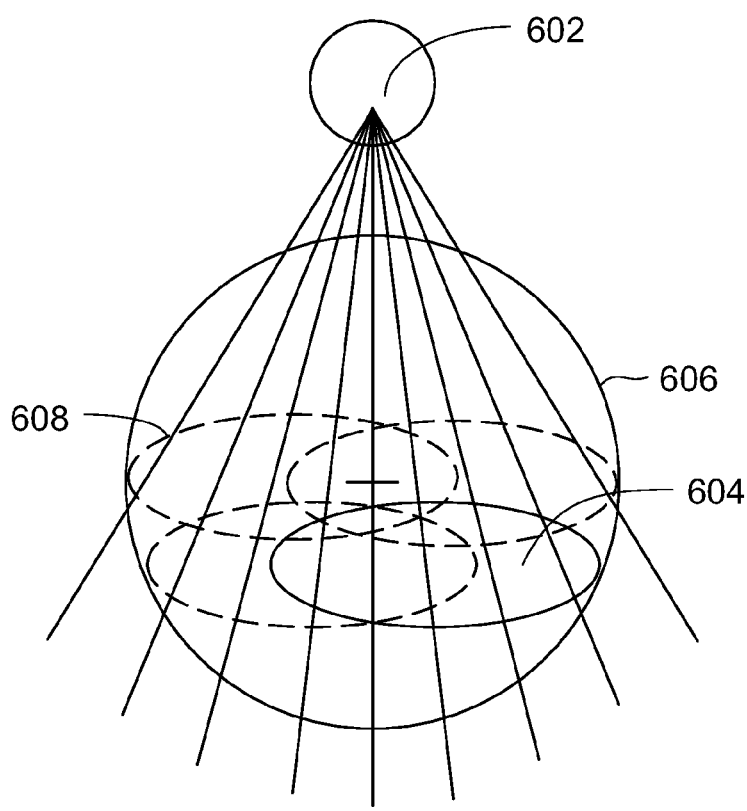
FIG. 6A shows four positions of a cylindrical phantom with an elliptical cross-section as used in an embodiment of the invention.

Reference is now made to FIG. 5, showing the sequence of acts in a calibration procedure according to some embodiments of the present invention. At 502 a phantom of known composition and shape is positioned at a first position in the bore of a CT scanner. FIG. 6A schematically shows X ray source 602 at a gantry rotation angle of 0°, and phantom 604, having an elliptical cross-section, positioned off the CT isocenter within bore 606. In this particular embodiment phantom 604 the elliptical cross section has major and minor axes of 400 mm and 150 mm and is positioned 75 mm to the right of the Isocenter and 100 mm below it, respective the orientation of FIG. 6A. In some embodiments phantom 604 is made of thermoplastic polymer such as polypropylene with density and radiation attenuation characteristics similar to those of the human body. The density of polypropylene is in the range of 0.85 to 0.95 g/cm³. In other embodiments the phantom is made of higher density polymer such as polyoxymethylene, known commercially as Delrin, wherein a given penetration length corresponds to higher attenuation. The density of Delrin is approximately 1.4 g/cm³.

Figure 6B:
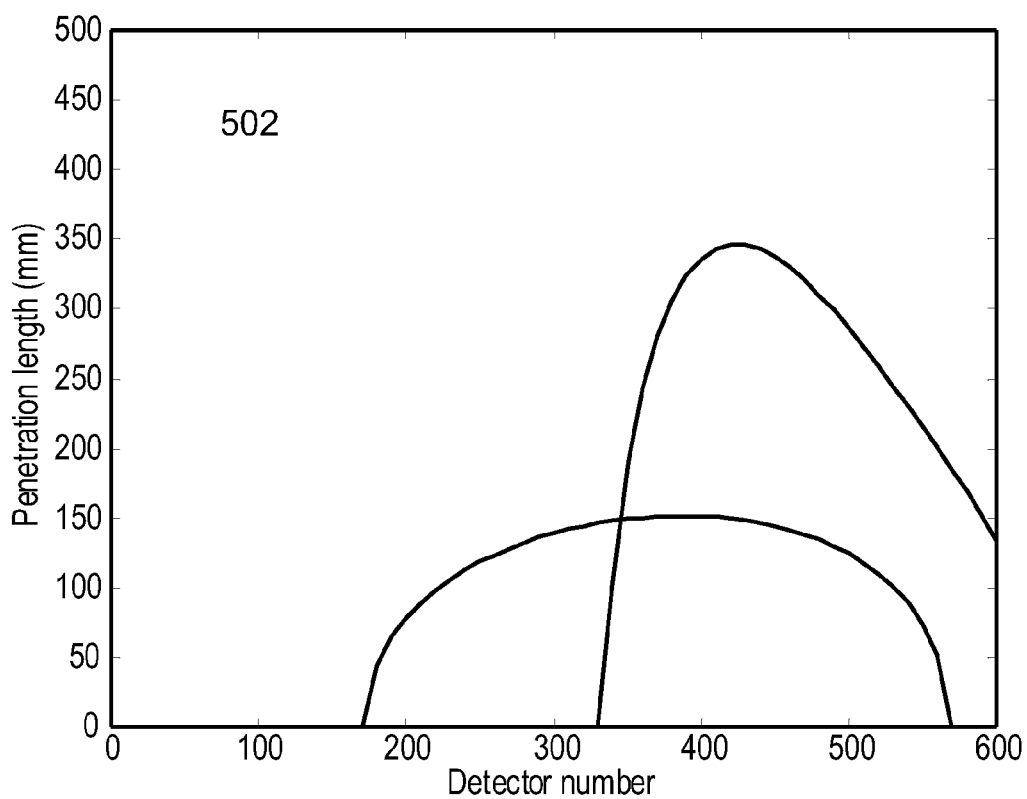
FIG. 6B shows expected penetration length a function of detector number for two angles of the source and detector for the shaded phantom position in FIG. 6A.

Returning to FIG. 5, at 504 attenuation data is acquired by irradiating the phantom and measuring the intensity of attenuated X rays by the scanner's detector array (not shown in FIG. 6A). In some embodiment the gantry is positioned at one particular or several gantry rotation angles and data is measured while the gantry is stationary at the particular rotation angle. In other embodiments data is taken while the gantry is rotating. Hereinbelow we refer to the set of attenuation data measured at one gantry angle as a "view". One advantage of measurements with a static gantry is the improved statistics that can be obtained for each measured view. FIG. 6B shows the length profile curves 610 and 612, corresponding to gantry angles of 0° and 90°, respectively.

Figure 7:
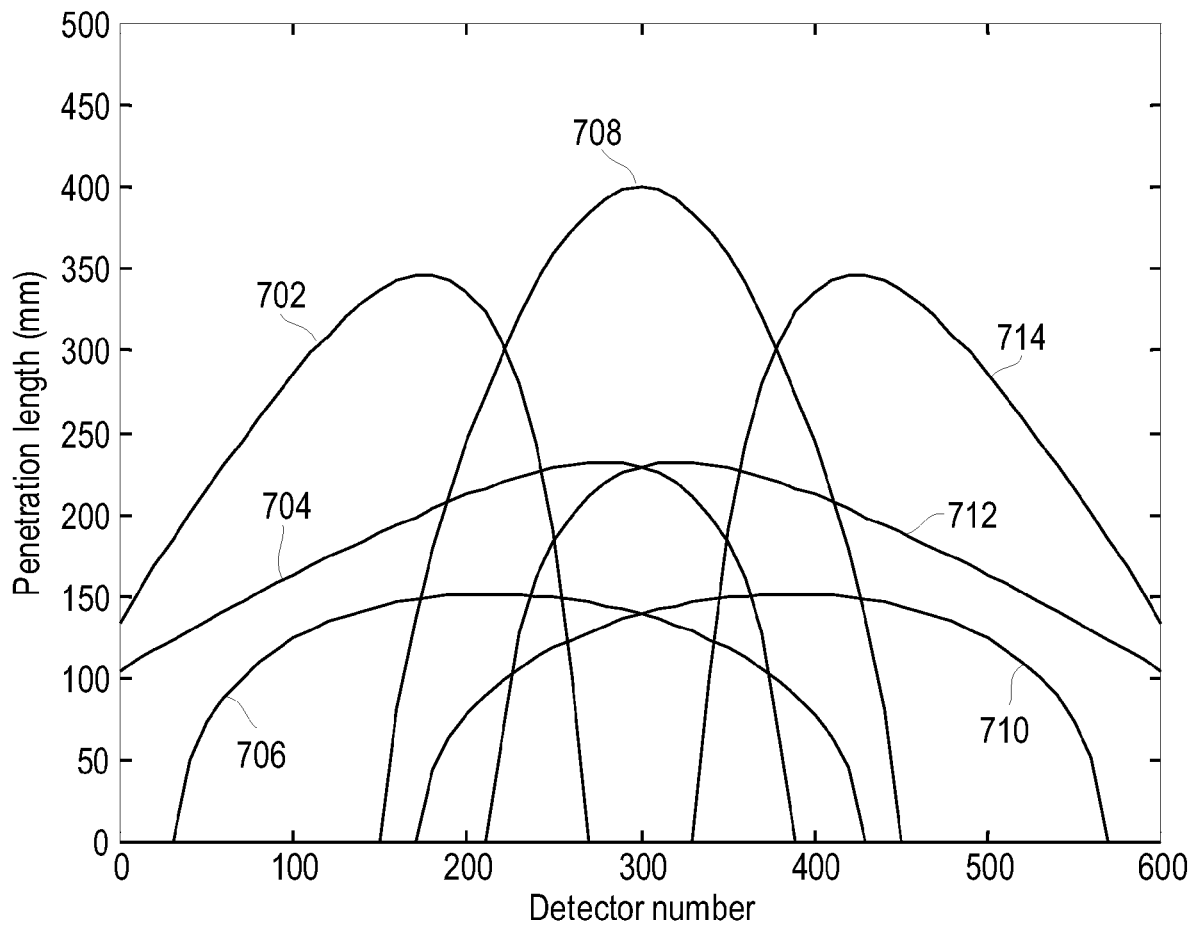
FIG. 7 shows expected penetration length a function of detector number for various angles of the source and detector for each phantom position in FIG. 6A.

As indicated in FIG. 5, blocks 502 and 504 are repeated one or more times, i.e., the phantom is moved to a second position and a second set of calibration data is measured at designated gantry angles. In some embodiments 502 and 504 of FIG. 5 may be repeated n additional times. FIG. 7 shows the length profiles obtained for the phantom 604 of FIG. 6A at four positions shown as full or dashed ellipses in FIG. 6A and a total of 7 gantry angles. In addition to the two measurements of FIG. 6B, the following measurements are taken: at 0° and 270° for phantom shift of 75 mm to the left of the isocenter and 100 mm down, 90° and 60° for phantom shift of 100 mm to the right and 300° for phantom shift of 100 mm to the left, all shifts respective the isocenter and the orientation of FIG. 6B. The seven views obtained in these measurements provide at least 3 useful calibration data points for each detector element in the range between detector numbers 40 to 560, covering the penetration length relevant for clinical body scans.

The phantom positions and the measurement angles of FIG. 6 and FIG. 7 demonstrate an embodiment of the present invention useful for particular CT scanners and particular clinical uses of the CT. Other embodiments may use other sets of positions and measurement angles, including optionally measurements at all view angles during a rotational scan. If all views are measured, then correction values for all attenuation values between zero and the maximum shown can be achieved. In some embodiments the phantom position relative to the isocenter is accurate to within two or one or less than one millimeter. In other embodiments the phantom is positioned only approximately at the designated position prescribed in the procedure. While the accuracy of phantom positioning affects the data processing steps described hereinbelow, in some cases the phantom position can be determined accurately enough from the acquired image.

Likewise, the present invention is not limited to ellipsoid phantoms. Other shapes of phantoms are possible in other embodiments of the invention. The phantom may be composed of a single density material or of multiple materials of different composition and density. For example, in some embodiments a circular phantom of density generally similar to water has an outer ring of higher density material such as PVC to simulate the radiation hardening characteristics of a human head. In some embodiments the phantom dimensions are accurate within two or one or less than one millimeter. In other embodiments the phantom dimensions are approximate.

Further, the embodiment of FIG. 6 and FIG. 7 prescribe the acquisition of calibration data set using a single phantom, providing a benefit of cost and weight relative to a procedure with multiple phantoms, in particular of a wide detector array. However, other embodiments may utilize more than a single phantom where at least one phantom is positioned in more than one position relative to the isocenter, still providing a more effective calibration data set than prior art methods using the phantoms at substantially a single position relative to the isocenter. In preferred embodiments of the invention, the phantom to be positioned at various positions is an elongate phantom. Table 1 shows the correlation between the reference numeral curves in FIG. 7 and the positions of the phantom and the distance from the iso-center (cross in the middle of FIG. 6A).

TABLE 1

| Reference | Gantry Angle (deg) | Horizontal shift (mm) | Vertical shift (mm) |
|---|---|---|---|
| 702 | 270 | −75 | −100 |
| 704 | 300 | −100 | 0 |
| 706 | 0 | −75 | −100 |
| 708 | 90 | 100 | 0 |
| 710 | 0 | 75 | 100 |
| 712 | 60 | 100 | 0 |
| 714 | 90 | 75 | −100 |

The output of block 504 in FIG. 5 is a set of views each with a corresponding set of attenuation data. As known in the art, in typical CT scanners the raw attenuation data is pre-processed prior to image reconstruction. In the discussion below we assume the attenuation data in the views are raw data which are normalized according to the X ray beam intensity, converted to logarithmic scale and subtracted from the air calibration pre-processed data, which is also on a logarithmic scale. However, the procedure may apply with appropriate adaptations also to un-processed raw data or to data pre-processed in a different way. The pre-processed attenuation data is not yet proportional to the attenuation length in the homogenous phantom because the calibration process discussed herein was not applied yet at this stage.

Below we describe by a way of example one possible procedure to generate scanner calibration tables out of the calibration view data.

The term "detection elements" as referred to herein mean the individual X-ray sensor elements and their associated data acquisition electronics. For clarity of the discussion a view is described as a one dimensional array containing the data of one detectors row. In a multislice detection array, the data for multiple rows is acquired simultaneously and the procedure described herein is applied to each of the rows separately.

Because of the variation in the spectral response of the different detection elements and because of statistical noise, the views obtained at block 504 of FIG. 5 have high frequency fluctuations from element to element. Statistical fluctuation are optionally reduced by acquisition over sufficient time with sufficient dose. At 506 of FIG. 5, the view data are smoothed to eliminate the fluctuations by any of several curve smoothing methods known in art. For example, smooth curves may be obtained by applying a low pass filter to the view data or by least square fitting an analytic function such as a third order polynomial to the view data.

At 508 of FIG. 5 the smooth curves are subtracted from the corresponding view data. The results are curves that display the residual deviation of each detector's or detectors group's response from the average response of neighboring detectors at a particular X ray attenuation level in the phantom, after normalizing the data by the air calibration tables during pre-processing. At 510 of FIG. 5 calibration tables are formed for each detector element from the relevant measured data. One known way to form detector's spectral response calibration tables is to store multiple pairs of correction values and associated attenuation levels (pre-processed view data) for each detector element. During imaging of a subject, an interpolated correction factor is generated for each data point from stored correction data, wherein the interpolation coefficients are determined from the data point's attenuation level versus the stored calibration attenuation levels. To the extent that more length profiles are taken, the amount of interpolation is reduced.

Another known way to form such calibration tables is to fit the multiple pairs of data of each detector element to analytical function, for example a second order polynomial, describing the correction factor versus attenuation level. The fitted coefficients are stored and used to calculate the corrections in a subject scan.

Referring to FIG. 7 as an example for a set of calibration curves obtained according to some embodiments of the present invention, we notice that none of the measured length profiles provides data that are useful to calibrate the entire detector array. Rather, during 510 of FIG. 5, calibration tables for different parts of the detector array are generated by using different views out of the set of measured views. The complete calibration table is composed of contributions from multiple phantom positions. Preferably, parts of the penetration profiles with very large slopes are not used for generation of calibration data since small errors can be magnified when the slope is high.

In further optional blocks 512 and 514 of FIG. 5 the measured data is used to generate over-all beam hardening calibration tables. At 512 the difference between the measured views and theoretical curves is determined The theoretical curves are calculated for example for the average beam energy based on the known phantom composition, dimensions and position in the scanner bore. The phantom position may be known from accurate positioning of the phantom or determined a-priory from the measured penetration profiles by observing the range of detectors shadowed by the phantom at multiple projection angles. Typically, an empirical normalization factor is applied to the theoretical curves to account for scanner specific parameters. This factor can be determined, for example, by acquiring view data for a relatively thin layer of absorber of known composition or under conditions of same absorption for the entire detector array.

In step 514 the difference between the measured curves and theoretical curves is used to generate calibration tables. In some embodiments this is done by fitting an analytical function, such as a second order polynomial, to the over-all available data of difference between theoretical and actual attenuation versus attenuation level. In such implementation, a single set of fit coefficients may be applicable to the entire detector array. In other embodiments separate correction coefficients are stored for each detector element In some embodiments the calibration tables achieved as described hereinabove in reference to blocks 510 and 514 of FIG. 5 are determined using particular phantoms and sets of measurement for imaging of specific human body parts. For example, images of human heads are corrected using calibration and correction data may be obtained on a phantom simulating the structure of a human head. One approach could be to have a separate phantom of lower dimensions (and optionally higher density) for the head, and use the multiple positions to achieve multiple calibration points for each detector, keeping in mind that for the head, only the detectors in the center area of the array need to be calibrated. Another approach could be to use same oblong or asymmetric phantom for body and head and use a different set of positions and/or view angles for the different body parts.

Another option is to use the same phantom for body and head (as described above) but insert a slab absorber of e.g. 5 to 10 mm PVC in front of the tube in head calibrations. This will pre-harden the beam to the same extent as the skull, Experts in the art will appreciate there are other possible ways to generate calibration tables and to apply said tables to imaging data. Such other ways are covered by the present invention in as much the acquisition of the calibration data follows blocks 502 and 504.

Figure 8A:
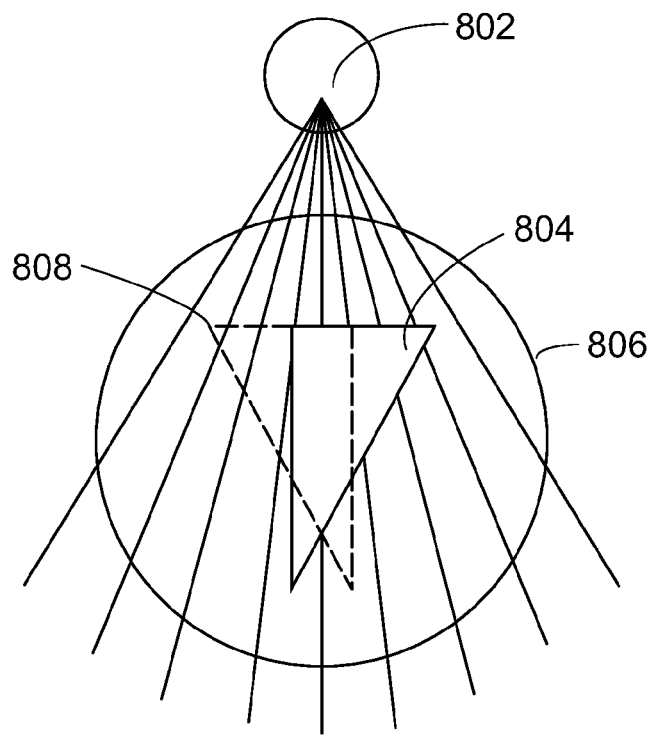
FIG. 8A schematically shows beam paths for a cylindrical phantom with a triangular cross-section in two different aspects.

Reference is now made to FIG. 8A, showing another embodiment of the present invention. X ray source 802 is shown at gantry rotation angle of 0°. In a first act corresponding to that of block 502 of FIG. 5, phantom 804 made of homogenous density material with a triangular cross section is positioned in a first position and orientation within gantry bore 806. In the particular example of FIG. 8A the phantom has a right angle triangular cross section, with one side of 250 mm and a perpendicular side of 450 mm. The right angle corner is positioned 200 mm above and 50 mm to the left of the scanner's isocenter, respective to the orientation of FIG. 8A. In an acquisition corresponding to block 504 of FIG. 5 a single or multiple sets of attenuation data are measured at a single or multiple gantry rotation angles. In this embodiment blocks 502 and 504 are repeated a second time with the phantom moved to a position and orientation shown as a dashed line 808 in FIG. 8B.

Figure 8B:
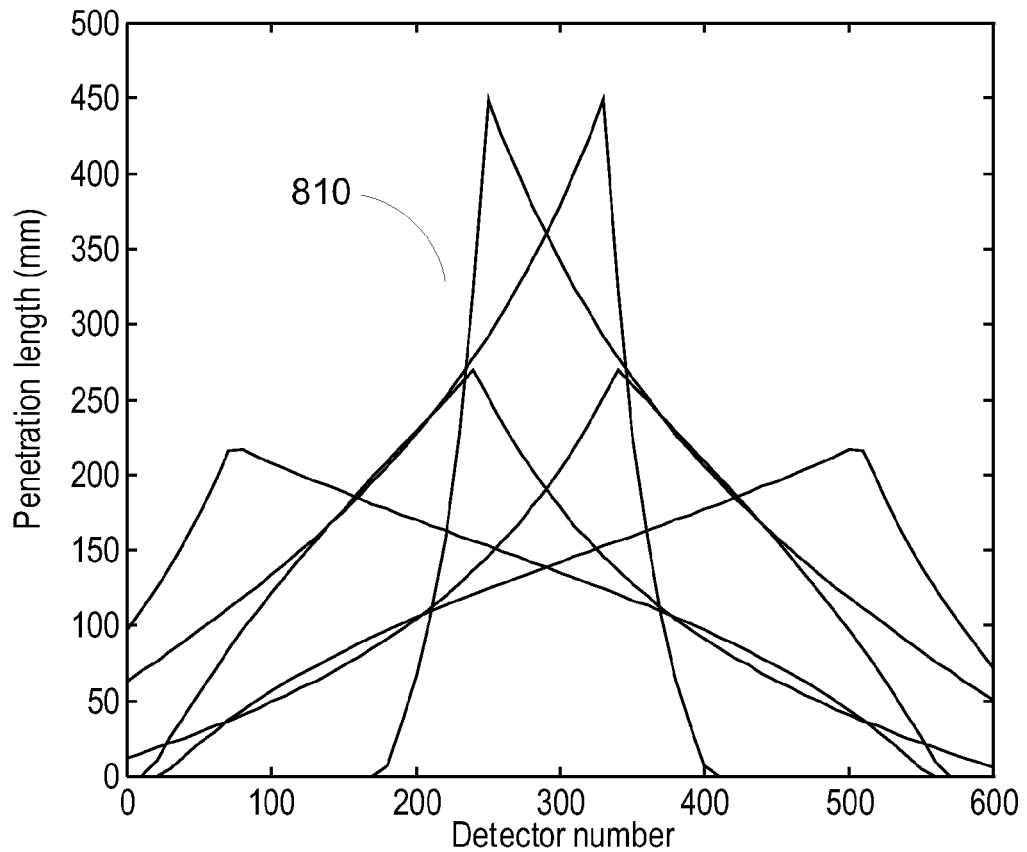
FIG. 8B shows expected penetration length as a function of detector number for three angles of source and detector for each of the aspects shown in FIG. 8A.

FIG. 8B provides the penetration length profiles 810 corresponding to three measurements at each phantom position and orientation. In the first position 804, measurements are taken at 0°, 90°, and 150°. In the second position 808, measurements are taken at 0°, 210°, and 270°. The calibration view data thus obtained are processed to generate scanner calibration and correction tables as described hereinabove in reference to blocks 504-514 in FIG. 5. However, for triangular phantoms or for other phantom cross sections with sharp corners, parts of the view data on or near discontinuity in the slope are excluded from the processing. The embodiment described in FIG. 8A and FIG. 8B is different than the embodiment described in FIG. 6A, FIG. 6B and FIG. 7 in that not only is the phantom asymmetric, but both the position and orientation of the phantom with respect to the scanner are changed. Orientation change of the phantom may involve rotation about an axis parallel to the scanner rotation axis as well as rotation about an axis perpendicular to the scanner rotation axis, which is the case in FIG. 8. Phantom 804 has an asymmetric cross section which may be beneficial in some embodiments.

Some embodiments are provided with a phantom holder capable of moving the phantom between different positions within the CT scanner bore (block 502 in FIG. 5). The phantom may be moved to various positions manually or automatically by a controller. Alternatively, in some embodiments the phantom is placed on or mounted to the patient support of the CT scanner. Typically, patient supports of CT scanners are capable of moving vertically responsive to a controller, enabling multiple phantom's positions along the vertical direction. For a non-round cross section phantom, vertical movement along with rotation of the phantom, e.g. by 90° about its center, and rotation of the gantry by same angle yield an effect equivalent to lateral movement. In order to change the phantom position both vertically and laterally respective the scanner bore without changing orientation, a mechanism for manual or automatic lateral translation of the phantom may be provided.

The calibration procedure is described in reference to FIG. 5 to FIG. 8 as applied for a row of detector elements. In CT scanners known in the art as multislice, multidetector, or cone beam scanners, there are multiple rows of detector elements and the method is applied to each of the detectors rows. Some embodiments of the invention use phantoms wide enough to cover the entire width of the detector respective the radiation source and calibration attenuation data are acquired for all rows at a time. In other embodiments the phantoms cover only a part of the width of the detector and calibration data are acquired for fewer than all of the rows at a time. Further, in some embodiments phantoms may have variable cross section along the direction parallel to the rotation axis of the scanner and different detector rows are subject to different penetration profiles during calibration measurements.

The invention is described herein in reference to specific phantoms, phantom positions and orientations, measurement view angles and data processing procedures. Experts in the art will appreciate the inventive method can be applied as well with different phantom shapes and compositions, phantom positions and orientations, measurement view angles and data processing procedures, and still be within the scope of the invention. The phantoms could, for example, be substantially identical circular phantoms sequentially placed at various positions. At least some of these may be offset from the central axis of the X-Ray beam.

While the invention is described with respect to cylindrical phantoms that have a uniform cross-section, the term "cylindrical" as used herein also includes cylindrical phantoms that vary in a stepwise manner in the axial direction, unless otherwise indicated.

Further, while the invention is described with respect to detector arrays comprising array of detector elements, the invention is applicable to detector arrays with discrete detector elements, detectors which are not divided into discrete elements, flat panel detectors of various types, single slice or multiple slice detector arrays, solid state or gas detectors and any other detectors useful for CT scanners.

Further, the inventive calibration procedure is described in reference to correction of X-ray spectral dependence of the detector elements' response and beam hardening effects. However, the method is applicable for correction of any effect wherein the response of said scanner detection system depends on the attenuation level of the X radiation, for example, scattering corrections.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. For example, the invention has been explained utilizing cylindrical phantoms. If a single detector row is to be calibrated (or for scanners having only a single row) the detector need only be of a length commensurate with the extent of the detector being calibrated during the scan or set of scans.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for calibration of a CT scanner having an x-ray source and a detector having an axial extent in the scanner, the source being rotatable about an epicenter between the source and detector, the method comprising:
   sequentially positioning a phantom having a non-circular cross section and a length commensurate with the extent of the detector at a plurality of positions between the X ray source and detector array of said CT scanner or sequentially positioning a plurality of phantoms each having a non-circular cross section and a length commensurate with the extent of the detector at a plurality of positions between the X ray source and detector array of said CT scanner;

acquiring calibration attenuation data for X rays that have been attenuated by traversing the phantom positioned at each of said plurality of positions; and calculating calibration corrections for CT scanner scan data from said calibration attenuation data.

2. The method according to claim 1 wherein said plurality of phantom positions comprises more than two positions.

3. The method according to claim 1 wherein said calibration attenuation data are acquired at multiple rotation angles of the source for at least one of said multiple phantom positions.

4. The method according to claim 1 wherein said calibration data are acquired while the X ray source of said CT scanner is static during acquisition of said calibration attenuation data.

5. The method according to claim 1 wherein said calibration data are acquired while the X ray source of said CT scanner is rotating about the scanner rotation axis during acquisition of said calibration attenuation data.

6. The method according to claim 1 wherein calibration data for different parts of the detector array are calculated from calibration attenuation data acquired at different phantom positions.

7. The method according to claim 1 wherein a same phantom or different ones of a plurality of phantoms having a same cross-section are placed at said plurality of positions used to obtain calibration tables for said CT scanner.

8. The method according to claim 1 wherein a plurality of phantoms of different cross-section are used to obtain calibration tables for said CT scanner.

9. The method according to claim 1 wherein said phantom has an elliptical cross section.

10. The method according to claim 1 wherein said phantom has a triangular cross section.

11. The method according to claim 1 wherein said phantom has an asymmetric cross section.

12. The method according to claim 1 wherein said phantom is positioned to within better than 2 mm relative to the rotation axis of said CT scanner.

13. The method according to claim 12 wherein said phantom is positioned to within better than 1 mm relative to the rotation axis of said CT scanner.

14. The method according to claim 1 wherein said phantom position is determined from the attenuation data.

15. A method according to claim 1 wherein said calibration corrections correct scan data for differences in the response of detector elements to X-rays.

16. A method according to claim 1 wherein said calibration corrections correct scan data for X-rays beam hardening effects.

17. A method according to claim 1 wherein said calibration corrections correct scan data for dependence of the response of said scanner detection system to the attenuation level of said X radiation.

18. A method according to claim 1 wherein at least a plurality of said positions are offset from said epicenter of the CT scanner.

19. A method for calibration of a CT scanner having an x-ray source and a detector array, the source being rotatable about an epicenter between the source and the detector, the method comprising:

sequentially positioning a same phantom or a plurality of essentially similar such phantoms at a plurality of positions between the X ray source and detector array of said CT scanner;

sequentially positioning a same phantom having a length commensurate with the extent of the detector at a plurality of positions between the X ray source and detector array of said CT scanner or sequentially positioning a plurality of essentially similar phantoms and a length commensurate with the extent of the detector at a plurality of positions between the X ray source and detector array of said CT scanner;

acquiring calibration attenuation data for X rays that have been attenuated by traversing the phantom positioned at each of said plurality of positions; and calculating calibration corrections for CT scanner scan data from said calibration attenuation data.

20. The method according to claim 19 wherein said plurality of phantom positions comprises more than two positions.

21. The method according to claim 20 wherein said calibration data are acquired while the X ray source of said CT scanner is rotating about the scanner rotation axis during acquisition of said calibration attenuation data.

22. The method according to claim 19 wherein said calibration attenuation data are acquired at multiple rotation angles of the source for at least one of said multiple phantom positions.

23. The method according to claim 19 wherein said calibration data are acquired while the X ray source of said CT scanner is static during acquisition of said calibration attenuation data.

24. The method according to claim 19 wherein calibration data for different parts of the detector array are calculated from calibration attenuation data acquired at different phantom positions.

25. The method according to claim 19 wherein said phantom has an elliptical cross section.

26. The method according to claim 19 wherein said phantom has a triangular cross section.

27. The method according to claim 19 wherein said phantom has an asymmetric cross section.

28. The method according to claim 19 wherein said phantom has a circular cross-section.

29. The method according to claim 19 wherein said phantom is positioned to within better than 2 mm relative to the rotation axis of said CT scanner.

30. The method according to claim 19 wherein said phantom position is determined from the attenuation data.

31. A method according to claim 19 wherein said calibration corrections correct scan data for differences in the response of detector elements to X-rays.

32. A method according to claim 19 wherein said calibration corrections correct scan data for X-rays beam hardening effects.

33. A method according to claim 19 wherein said calibration corrections correct scan data for dependence of the response of said scanner detection system to the attenuation level of said X radiation.

* * * * *